Figure 1:
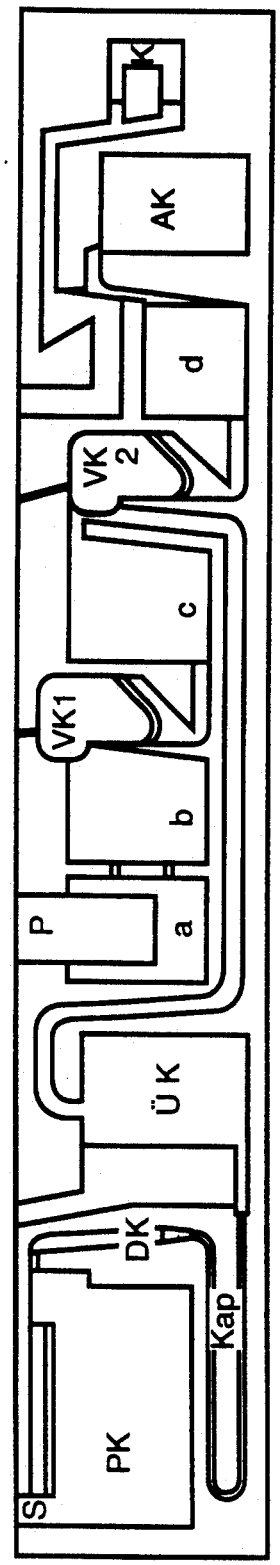

United States Patent [19]

Hübner-Parajsz et al.

[11] Patent Number: 5,248,593
[45] Date of Patent: Sep. 28, 1993

[54] PROCESS AND REAGENT FOR THE DETERMINATION OF THE LUTEINISING HORMONE AND MONOCLONAL ANTIBODIES SUITABLE THEREOF

[75] Inventors: Christa Hübner-Parajsz, Tutzing; Hartmut Schetters, Neufahrn; Helmut Lenz, Tutzing; Klaus Erler, Pöcking, all of Fed. Rep. of Germany

[73] Assignee: Boehringer Mannheim GmbH, Mannheim, Fed. Rep. of Germany

[21] Appl. No.: 908,535

[22] Filed: Jun. 29, 1992

Related U.S. Application Data

[63] Continuation of Ser. No. 833,996, Feb. 27, 1986, abandoned.

[30] Foreign Application Priority Data

Mar. 6, 1985 [DE] Fed. Rep. of Germany ....... 3507848

[51] Int. Cl.$^5$ .............................. C12Q 1/00
[52] U.S. Cl. ................... 435/7.9; 435/7.93; 435/7.95; 435/70.21; 435/240.27; 436/536; 436/548; 530/388.1; 530/388.24; 530/388.15
[58] Field of Search ........... 530/388.1, 388.15, 388.24; 435/70.21, 240.27, 7.9, 7.93, 7.95; 436/536, 548

[56] References Cited

U.S. PATENT DOCUMENTS 4,722,899 2/1988 Hamaoka et al. ................... 435/240
4,792,528 12/1988 Canfield et al. ..................... 436/548

FOREIGN PATENT DOCUMENTS 2111201 6/1983 United Kingdom .

OTHER PUBLICATIONS

Chow et al., Chemical Abstracts, 103:116420m, 940 (1985).
Rathnam et al., Clin. Chem. 30(5):665–671, "A Sandwich Solid-Phase Enzyme Immunoassay For Lutropin In Urine", (May 1984).
Sevier et al., Clin. Chem: 27(11); 1797–1806, "Monoclonal Antibodies In Clinical Immunology", (1981).
Federici et al., Federation Proceedings, 41(3): 596, Abstract 1907, "Production and Characterization of Monoclonal Antibodies To Human Luteinizing Hormone"(1982).
Soos et al., Chem. Abst. vol. 99 (1983), p. 187909n.

Primary Examiner—Sam Rosen
Attorney, Agent, or Firm—Felfe & Lynch

[57] ABSTRACT

The present invention provides an immunological process for the determination of the luteinising hormone (LH), wherein at least one monoclonal antibody is used which is directed against LH and cross-reacts with other glycoprotein hormones to an extent of less than 3%.

The present invention also provides a reagent for the determination of the luteinising hormone, wherein it contains at least one monoclonal antibody which is directed against LH and cross-reacts with other glycoprotein hormones to an extent of less than 3%.

Furthermore, the present invention provides a monoclonal antibody against the luteinising hormone and a process and a hybridoma cell line for producing it.

33 Claims, 2 Drawing Sheets

PROCESS AND REAGENT FOR THE DETERMINATION OF THE LUTEINISING HORMONE AND MONOCLONAL ANTIBODIES SUITABLE THEREOF

This application is a continuation, of application Ser. No. 833,996, filed Feb. 27, 1986, now abandoned.

The present invention is concerned with a process and a reagent for the determination of the luteinising hormone, as well as with monoclonal antibodies suitable therefor.

The determination of the luteinising hormone (LH) in body fluids, for example urine, serum and plasma, is mainly employed in order to be able to assess the endocrinological status of the hypthalamus, hypophysis and gonads. These investigations serve, in particular, for the differential diagnosis of hypogonadism, infertility and the like. In addition, the LH determination is used in order to determine the ovulation time point in the case of an induction of pregnancy.

In all these cases, the serum values lie within the physiological range. Furthermore, the concentration of LH in the serum is also measured solely for the purpose of obtaining evidence regarding the biological effectiveness of this hormone. Of diagnostic importance is, therefore, essentially a knowledge of the serum level of the native hormone.

The physiological concentration of human LH in the serum lies in the following ranges:

| | |
|---|---|
| men | 4–24 mIU/ml. |
| women before menopause, cycle | 10–20 mIU/ml. |
| women ovulation peak | 80–100 mIU/ml. |
| women after menopause | 80–150 mIU/ml. |

For the determination of LH, there are especially suitable immunological test processes in which the hormone is determined as antigen with one or more antibodies directed against it. The obtaining of antibodies with these polypeptide hormones involves difficulties since all polypeptide hormones are poorly immunogenic. Because of the homology between LH and other glycoprotein hormones, for example the follicle-stimulating hormone (FSH), thyreotropin-stimulating hormone (TSH) and human chorionic gonadotropin (hCG), it is very difficult to obtain specific antibodies against one of these hormones. An antibody directed against one of these glycoprotein hormones usually displays more or less cross-reactivity with the other glycoprotein hormones.

Clinica Chemica Acta 133, 263–274/1983 describes monoclonal antibodies against LH which cross-react with TSH and hCG up to 10% and with FSH up to 3%. British Patent Specification No. 2,111,201 also describes a monoclonal antibody against LH. However, this reacts just as well with hCG. A monoclonal antibody which is specifically directed against LH and displays no cross-reactivity with the other glycoprotein hormones is hitherto not known. Therefore, at the moment, it is not possible to determine LH immunologically without other glycoprotein hormones being more or less included.

It is an object of the present invention to provide a new immunological process and reagent with the help of which LH can be specifically determined even in the presence of other glycoprotein hormones.

Thus, according to the present invention, there is provided an immunological process for the determination of the luteinising hormone (LH), wherein at least one monoclonal antibody is used which is specifically directed against LH and cross-reacts with other glycoprotein hormones at an extent of less than 3%.

The present invention also provides a reagent for the determination of the luteinising hormone, wherein it contains at least one monoclonal antibody which is directed against LH and cross-reacts with other glycoprotein hormones to an extent of less than 3%.

As immunological determination methods, there can, in principle, be used all available immuno-assays, such as radio-immuno-assay, enzyme-immuno-assay, fluorescence-immuno-assay and the like. Furthermore, all process variants, such as competitive immunoassay, sandwich process and the like can be used. For labelling, there can be used the agents which are conventional for the particular determination methods. Thus, in the case of a radio-immuno-assay, there are used radioisotopes, for example $^{125}I$, for the labelling. For an enzyme-immuno-assay, there can be used all enzymes usually employed for this purpose, for example peroxidase or $\beta$-galactosidase. For a fluorescence-immuno-assay, the usual fluorescing groups can be used as labels. Details of these various test methods and process variants are well known. Test variants are advantageous in which at least two monoclonal antibodies according to the present invention are employed which are directed against different antigenic determinants of the LH and at least one of which cross-reacts with other glycoprotein hormones to an extent of less than 3%.

For the determination of LH, it has proved to be especially preferable to use the sandwich process in which the antigen to be determined is brought into contact with a carrier-bound and a labelled antibody. For such a determination process, a specific monoclonal antibody according to the present invention can, for example, be bound to the solid phase. In a first incubation step, this is incubated with the sample which contains the LH to be determined, as well as, in general, other glycoprotein hormones, LH thereby being selectively bound by the specific antibody. After the usual washing step, it is incubated with the labelled antibody. This must not necessarily be specifically directed against LH but can also cross-react with other glycoprotein hormones.

The process can also be carried out with a non-specific carrier-bound antibody. However, it is then necessary that, as labelled antibody, there is employed an antibody according to the present invention which is directed specifically against LH.

Variants of the sandwich process can also be used for the determination of LH. Thus, for example, a soluble sandwich complex can first be formed with a non-labelled, soluble antibody and the labelled antibody. This is subsequently made insoluble with the help of a carrier-bound antibody which is directed against the Fc$\gamma$ part of the non-labelled soluble antibody. In the case of this process variant, at least the non-labelled, soluble antibody must be an antibody according to the present invention. The labelled antibody is thereby preferably employed in excess.

The essence of the present invention is to be seen in that it is, surprisingly, possible to make available for these immunological processes monoclonal antibodies which are specifically directed against LH and which, therefore, make possible a specific determination of LH.

Therefore, the present invention also provides monoclonal antibodies against LH, the cross-reactivity of which with other glycoprotein hormones amounts to less than 3%.

For obtaining the monoclonal antibodies according to the present invention, experimental animals, for example mice, are immunised with LH. For the immunisation, the immunogen is administered in the usual way, for example in combination with an adjuvant. As adjuvant, it is preferred to use aluminium hydroxide, together with *Bordetella pertussis* or Freund's adjuvant. The immunisation preferably takes place over several months with at least four immunisations at 4 to 6 week intervals (intraperitoneal injection).

From thus immunised animals are obtained B-lymphocytes which are fusioned with a permanent myeloma cell line. The fusioning takes place according to the known process of Kohler and Milstein (Nature 256, 495-497/1975). The primary cultures of hybrid cells thereby formed are cloned in the usual way, for example with the use of a commercially available cell sorter or by "limiting dilution". In each case, those cultures are further worked up which, in an appropriate test process, for example an enzyme-immuno-assay (ELISA process), react positively against LH and negatively or only a little with the other glycoprotein hormones. There are thus obtained several hybridoma cell lines which produce the monoclonal antibodies according to the present invention. According to known methods, these cell lines can be cultured and those of them producing monoclonal antibodies are isolated.

By way of example, for cell lines obtained in this way, there are mentioned:

| clone 369 | (NCACC 84122001) and |
|-----------|----------------------|
| clone 799 | (NCACC 84122005).    |

The cell lines have been deposited under the given number at the NCACC depository (National Collection of Animal Cell Cultures). The cell lines are available to one determined by the Commissioner to be entitled thereto under 35 V.S.C. §122; 37 C.F.R. §1.14.

The so obtained monoclonal antibodies have a very high affinity (affinity constants of the order of magnitude of $10^9$ to $10^{11}$ 1/mol as determined following Scatchard, *Ann. N.Y. Acad. Sci.* 51:660 (1949)) against LH and cross-react with other glycoprotein hormones to an extent of less than 3%. Preferred monoclonal antibodies display a cross-reactivity towards other glycoprotein hormones, such as hCG, FSH and TSH, of less than 1% and especially of less than 0.1%. For the determination of the affinity and of the cross-reactivity with other hormones, there can be used the processes known for this purpose.

The monoclonal antibodies according to the present invention are outstandingly useful for the specific determination of the hormone LH in the presence of other glycoprotein hormones in a sample, for example serum or plasma. For these determination processes, there can be used the monoclonal antibodies as such or fragments thereof which possess the corresponding immunological properties, for example Fab fragments. Therefore, the expression "monoclonal antibodies" is to be understood to mean not only the complete antibodies but also the fragments thereof.

The following Examples are given for the purpose of illustrating the present invention:

EXAMPLE 1

Obtaining of monoclonal antibodies against LH

Balb/c mice, 8-12 weeks old, are immunised intraperitoneally with 100 μg. hLH (obtainable from Immunex), adsorbed on aluminium hydroxide and *Bordetella pertussis*. After 6 weeks, three further immunisations are carried out at 4 week intervals. 50 μg. LH, adsorbed on aluminium hydroxide and *Bordetella pertussis*, are thereby, in each case, administered intraperitoneally.

About four months after the last immunisation, fusioning is carried out. Four days and three days before fusioning, in each case, immunisation is carried out again with 100 μg. LH/PBS (phosphate buffered saline) intraperitoneally or intravenously.

For the fusioning, with reference to the method described by Galfre (Methods in Enzymology, 73, 3/1981) $10^8$ spleen cells of an immunised mouse are mixed once with $2 \times 10^7$ myeloma cells (P3×63Ag8-653, ATCC-CRL 8375) and subsequently centrifuged for 10 minutes (300 g, 4° C.). The cells are again washed once with BSS (balanced salt solution) and centrifuged at 400 g. The supernatant is removed. The cell sediment is mixed with 1 ml. 50% PEG solution (M.W. 4000, Merck). Thereafter, at ambient temperature, 5 ml. RPMI 1640 medium (RPMI=Rosewell Parker Memory Institute) without foetal calf serum (FCS) and subsequently once again 5 ml. RPMI 1640 medium with 10% FCS, are slowly added dropwise thereto, the mixture is made up with medium to 50 ml. and centrifuged for 10 minutes at 400 g. The sedimented cells are taken up in RPMI 1640 medium with 10% FCS. $2 \times 10^5$ spleen cells are each seeded into 24 well cell culture plates (obtainable from Nunc). To each culture are added $1 \times 10^5$ spleen cells or $5 \times 10^4$ peritoneal exudate cells as feed cells. On the following day, hypoxanthine-azaserine selection medium (100 mM hypoxanthine, 1 μg./ml. azaserine) is added thereto.

After about 7-10 days, many clones are already visible. The supernatent of the primary cultures is tested according to the ELISA process described in Example 2. Primary cultures which contain antigen-specific antibodies are further cloned with the help of a fluorescence-activated cell sorter on 96-well culture plates (obtainable from Nunc). As feed cells, there are used $1 \times 10^4$ peritoneal exudate cells or $2 \times 10^4$ spleen cells per 96-well of the culture.

In this way, there can be isolated the two hybridoma cell lines of clone 369 and clone 799, which have been deposited at the NCACC depository (National Collection of Animal Cell Cultures) under the deposit numbers:

| NCACC 84122001 | (clone 369) and |
|----------------|-----------------|
| NCACC 84122005 | (clone 799).    |

For the production of ascites, $5 \times 10^6$ hybrid cells are injected intraperitoneally to mice which had previously been pre-treated 1 to 2 times with 0.5 ml. pristane. One to three weeks thereafter, ascites fluid can be obtained from the mice and the antibodies can be isolated herefrom in the usual way. These monoclonal antibodies are specifically directed against LH and show no or only a small cross-reactivity with other glycoprotein hormones. In the following, they are designated as MAB 369 (from clone 369) and MAB 799 (from clone 799).

The two monoclonal antibodies belong to the subclass IgG1/K. They possess the following affinities:
MAB 369 = $7.9 \times 10^{10}$ 1/mol
MAB 799 = $9.5 \times 10^{11}$ 1/mol.

For the determination of the affinities, competition curves are determined with the homologous antigen according to the method of Scatchard (Ann. N.Y. Acad. Sci. 51, 660/1949) and evaluated. The measurements necessary therefor are carried out analogously to Example 2.

EXAMPLE 2

Screening test on antibodies against LH

In order to recognise the presence and specificity of antibodies against LH in the serum of immunised mice or in the culture supernatant of the hybrid cells or in ascites, there is used an ELISA process as test principle: Microtitre plates are coated overnight with 1 μg. LH/ml. of coating buffer (0.2M sodium carbonate/bicarbonate, pH 9.3-9.5) at 37° C. and then after-treated for 10 minutes with 0.9% sodium chloride solution and 1% albumin solution and subsequently washed with 0.9% sodium chloride solution. Subsequently, incubation is carried out at 37° C. for one hour with 100 μl. of sample and again washed with 0.9% sodium chloride solution. There follows a further incubation for one hour at 37° C. with 100-150 mU/ml. of a sheep anti-mouse-IgG-peroxidase conjugate. After a further washing step with 0.9% sodium chloride solution, the peroxidase activity is determined in the usual way (for example with ABTS, 30 minutes at ambient temperature, there being read off the extinction difference, Δ mE, at 405 nm).

The ELISA test can also be carried out as follows:

The microtitre plates are first coated with a sheep anti-mouse IgG (20-30 μg./ml. coating buffer, one hour to overnight, 37° C.). Thereafter, further treatment is carried out as described above, the sample solution is added and again washed. Finally, incubation is carried out with 250 mU/ml. of an LH-peroxidase conjugate for 1 hour at 37° C. After again washing, the peroxidase activity is determined, for example with ABTS.

EXAMPLE 3

Determination of the cross-reactivity with other glycoprotein hormones

The procedure described in Example 2 is used. The reactivity of LH is first determined. Then, to the particular monoclonal antibodies, there is, in each case, added the antigens (hCG, TSH, FSH) to be tested for cross-reaction, in increasing concentration.

The cross-reactions are subsequently calculated according to the following equation:

$$\frac{C(LH)}{C(\text{cross-reacting antigen})} \times 100 = \% \text{ cross-reaction}$$

C = concentration of the antigen which is necessary for the achievement of 50% of the maximum signal In the following Table 1 are set out the measured values for MAB 369 and MAB 799:

TABLE 1

Cross-reaction of the monoclonal antibodies MAB 369 and MAB 799 against LH with hCG, FSH and TSH

| glyco-hormone | origin (Firm) | max. conc. in the serum | conc. range in the test to cross-reaction | MAB 369 % cross react. | MAB 799 % cross react. |
|---|---|---|---|---|---|
| hCG | UCB Belgium | 200 IU/ml. | 0-250 IU/ml. | <0.1 | <0.1 |
| FSH | UCB Belgium | 400 mIU/ml. | 0-9 IU/ml. | <0.1 | <0.1 |
| α-TSH | Boehringer Mannheim | 1000 μIU/ml. | 0-9000 μIU/ml. | <0.1 | <0.1 |
| β-TSH | Boehringer Mannheim | 1000 μIU/ml. | 0-9000 μIU/ml. | <0.1 | <0.1 |

EXAMPLE 4

Determination of epitope specificity

A microtitre plate is coated for 2 hours at 37° C. or overnight at 4° C. with 10 μg./ml. sheep antibody against the Fcγ region of a mouse antibody in 0.2M carbonate buffer (pH 9.6). Thereafter, it is washed with PBS/0.1% Tween 20 (pH 7.35). Subsequently, there are added thereto 100 μl. of a monoclonal antibody (MAB 1, concentration 10 μg./ml.) in incubation buffer (PBS, 0.1% bovine serum albumin (BSA), 0.1% Tween 20) and incubated for 2 hours at 37° C.

An LH-peroxidase conjugate (100 mU/ml.) is pre-incubated overnight with 10 μg./ml. of a second monoclonal antibody (MAB 2) in solution at 4° C.

After the incubation of the plate with MAB 1, excess MAB 1 is removed by washing with PBS-Tween 20. The plate is then after-coated for 30 minutes at ambient temperature with 1% mouse normal serum in FBS-BSA. 100 μl. of the pre-incubated MAB 2/LH-peroxidase complex are applied to the plate and incubated for 2 hours at 37° C. The bound peroxidase activity is made visible with ABTS as substrate. The measured colour intensity is directly proportional to the MAB 2/LH-peroxidase conjugate bound to MAB 1. For MAB 799 as MAB 1 and MAB 369 as MAB 2, the bound activity amounts to 34% of the non-competing LH-POD activity.

The results found show that the two monoclonal antibodies are directed against two different epitopes of the antigen LH.

EXAMPLE 5

Determination of LH

A) Preparation of the reagent solutions
1) Substrate buffer:
15 mM sodium phosphate buffer, pH 7.4
15 mM sodium chloride
5 mM EDTA
0.2% bovine serum albumin, pH 7.4
5 mM o-nitrophenylgalactoside
2) Receptor 1 solution:
As receptor 1, there is employed a monoclonal mouse anti-hLH antibody according to the present invention. The ascites fluid containing this antibody is mixed ad 1.8M with ammonium sulphate. The precipitate is taken up in a buffer of 15 mM sodium phosphate (pH 7.0) and 50 mM sodium chloride. The solution so obtained is subjected to a passage over DEAE-cellulose.
3) Receptor 3 solution:

As receptor 3, there is also employed a monoclonal mouse anti-hLH antibody according to the present invention which, however, recognises a different antigenic determinant than receptor 1. The ascites fluid containing this antibody is purified as described in 2) above. The complete antibody is split up in known manner into the Fab fragment. The Fab fragments obtained are coupled with β-galactosidase according to the method of R. R. Porter (Biochem. J., 73, 119/1959).

4) Activated receptor 2 solution:

Sheep anti-mouse Fcγ antiserum is mixed ad 1.8M with ammonium sulphate. The precipitate is taken up in a buffer of 15 mM sodium phosphate (pH 7.0) and 50 mM sodium chloride. The solution so obtained is subjected to a passage over DEAE-cellulose.

B) Production of reagent carriers

1) Reagent carrier 1:

40 μl. of a solution which contains, per ml.

100 μmol sodium phosphate (pH 7.3, 37° C.),

2 μmol magnesium chloride, 0.9% sodium chloride, 0.5% bovine serum albumin,

5 μg./ml. anti-hlH monoclonal antibodies from mouse (receptor 1 solution)

100 mU anti-hLH antibody (mouse) Fab fragment-β-galactosidase conjugate (receptor 3 solution)

is applied dropwise to a fleece which consists of commercial polyester paper. Subsequently, it is dried at ambient temperature. Until used, these fleece are stored at 4° C. and at a relative atmospheric humidity of 20%.

2) Reagent carrier 2:

Sheep antibodies against the Fcγ part of mouse antibodies (activated receptor 2 solution) are fixed on to cellulose fleece according to the known cyanogen bromide activation process (see Federal Republic of Germany Patent Specification No. 1768512), whereby, per g. of fibre material, there are provided 10 μg. of antibody for fixing. Uncoupled antibody is removed by washing and the fleece is gently dried at ambient temperature. The so obtained fleece is stored analogously to reagent carrier 1.

The determination with the help of these two reagent carriers 1 and 2 takes place with the use of the device for carrying out analytical determinations described in U.S. Pat. No. 4,690,899. This describes a rotor insert element for centrifugal automatic analysers comprising a formed body which contains a sample application chamber, which is in connection with a plurality of reagent fields, each of which contains an adsorbent carrier material impregnated with a particular reagent, at least one mixing valve chamber and a measurement chamber which together from a sample liquid transport path which leads from radially inwardly to radially further outwardly when the insert element is fixed on the rotor and also has at least one further chamber for the reception of a liquid and a transport path which leads from this chamber to the measurement chamber and is at least partly identical with the sample liquid transport path. The sample liquid transport path thereby leads from a sample application chamber (P) via a chamber (a) filled with absorbent material containing buffer, a chamber (c) and a first valve chamber (VK1) arranged between the chambers (a) and (c), to a second valve chamber (VK2) and from this, via a chamber (d) and via a collection chamber (AK), to a measurement chamber (K). An additional chamber (b) is shown which does not participate in the process described herein. For the reception of a further liquid, there is provided a substrate chamber (PK) having a substrate application port (s) constructed as pump chamber which is connected with the second valve chamber (VK2) via a dosing device comprising a dosing chamber (DK) and a capillary (Kap), and an overflow chamber (UK). FIG. 1 of the accompanying drawings shows schematically the rotor insert element used. Reagent carrier 1 is hereby placed on field c of the disposable insert element and reagent carrier 2 in field d. 40 μl. of sample are thereby pipetted through an opening on the upper edge directly on to the field a. The sample is undiluted. 270 μl. of substrate solution are pipetted into chamber PK. By means of an appropriate programme, where high speeds of rotation alternate with stopping, sample and substrate solution are then conveyed in the direction of the separation matrix and cuvette. In the course of the programme, the receptors 1 and 3 are thereby eluted by the sample liquid from the field c and the homogeneous mixture is subsequently brought to reaction. On field d, the complexes formed are bound to the receptor 2. The transfer of the sample from field c to field d takes place within a very short period of time.

The substrate solution is divided into portions by the dosaging chamber KD, the first of which serves for washing out excess, non-complexed conjugate.

The β-galactosidase activity bound to d via complex formation is proportional to the amount of hLH contained in the sample. This activity is determined with a further substrate portion, the substrate thereby being reacted in a 5 minute reaction to give coloured products. The colour formed is measured in the cuvette at 410 nm.

Figure 2:
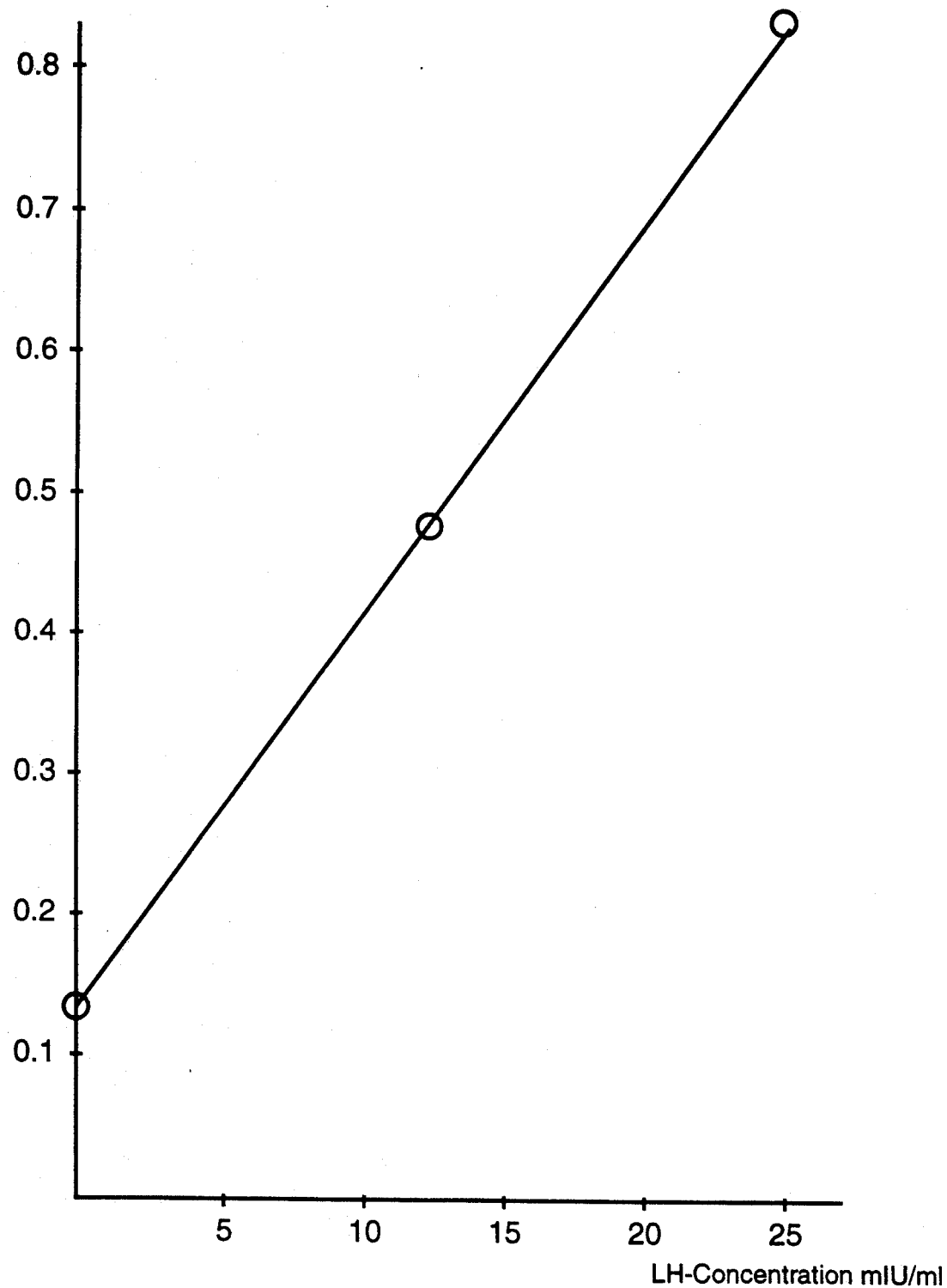

The calibration curve according to FIG. 2 of the accompanying drawings is obtained from calibration sera of known LH content which cover the range from 0 to 25 mU hLH/ml. (standardised according to the first IRP standard for hLH 68/40) and makes possible a sufficiently sensitive measurement of hLH in serum or plasma. On the basis of this calibration curve, there can be determined the unknown content of hLH in body fluids, for example serum or sample. The finding again of standards made up with 100 IU/ml. hCG (1st IRP=1st international reference preparation of WHO) amounts to 96 to 104%.

EXAMPLE 6

Determination of LH according to the sandwich principle

100 μl. of a solution which contains a monoclonal antibody against LH according to the present invention in a coating buffer (0.2M sodium carbonate/bicarbonate, pH 9.4) in a concentration of 50 μg./ml., are introduced into each recess of a microtitre plate and incubated for one hour at ambient temperature. Subsequently, it is after-coated with incubation buffer (1% bovine serum albumin, 0.9% sodium chloride) and incubated for 30 minutes at ambient temperature. After washing with wash buffer (0.9% sodium chloride, 0.1% Tween 20), there are introduced into each recess 100 μl. of sample which contains the LH to be determined and incubated for 30 minutes at ambient temperature. After again washing with wash buffer, it is loaded with 100 μl. of a conjugate of peroxidase (activity 100 mU/ml.) and a further monoclonal antibody according to the present invention which, however, is directed against a different epitope of LH and incubated for 1 hour at ambient temperature.

For the preparation of the conjugate, there is used horseradish peroxidase (EC 1.11.1.7). The conjugate is prepared by oxidation with periodate and subsequent reduction with boron hydride according to the procedure of P. K. Nakane (M. B. Wilson and P. K. Nakene, in W. Knapp ed. "Immunofluorescence and Related Staining Techniques", 1978, Elsevier/North Holland, Biomedical Press, pages 215-224).

After washing with wash buffer, it is loaded with 100 μl. ABTS substrate solution and, after a one hour colour reaction, the extinction is measured at 405 nm in an ELISA reader (Dynatec).

For the production of a calibration curve, in the case of the above-described process, instead of the sample, solutions are used which contain LH in different, definite concentrations.

It will be understood that the specification and examples are illustrated but not limitative of the present invention and that other embodiments within the spirit and scope of the invention will suggest themselves to those skilled in the art.

We claim:

1. Hybridoma cell line which produces monoclonal antibodies which specifically bind to luteinising hormone and cross react with TSH, HCG and FSH to an extent of less than 3% as determined using an enzyme linked immunosorbent assay, said cell line prepared by
    (i) intraperitoneally immunizing a host animal with human luteinizing hormone;
    (ii) removing the spleen of said host animal;
    (iii) fusing cells of said spleen with myeloma cells;
    (iv) separating fused cells from non-fused cells by culturing in selection medium;
    (v) screening supernatant of fused cells for production of antibodies by mixing said supernatant with human luteinizing hormone to bind antibody in said supernatant to human luteinizing hormone and with labelled antibody against antibodies which bind to human luteinizing hormone to identify said human luteinizing hormone binding antibodies, and
    (vi) repeating step (v) with a glycoprotein hormone selected from the group consisting of TSH, HCG and FSH and with a labelled antibody, to determine human luteinizing hormone specific antibodies which cross react to an extend less than 3% with said glycoprotein hormone.

2. The hybridoma cell line of claim 1, comprising a cell line deposited at the National Collection of Animal Cell Cultures under deposit number NCACC 84122001.

3. The hybridoma cell line of claim 1, comprising a cell line deposited at the National Collection of Animal Cell Cultures under deposit number NCACC 84122005.

4. Monoclonal antibody produced by the hybridoma cell line of claim 1.

5. The monoclonal antibody of claim 4, which cross reacts with TSH, HCG and FSH to an extent less than 1%.

6. The monoclonal antibody of claim 4 comprising MAB 369.

7. The monoclonal antibody of claim 4 comprising MAB 799.

8. Process for the determination of the presence of luteinizing hormone (LH) comprising contacting a sample with at least one monoclonal antibody of claim 4, under conditions favoring formation of monoclonal antibody-antigen complexes between said monoclonal antibody and LH and determining the presence of said complexes.

9. Process of claim 8 comprising monoclonal antibody MAB 369 or MAB 799.

10. Process of claim 8 comprising monoclonal antibodies MAB 369 and MAB 799.

11. Process of claim 8 wherein at least one monoclonal antibody is used which specifically binds to LH and cross reacts with TSH, HCG, and FSH to an extent of less than 1%.

12. Process of claim 8, wherein at least two monoclonal antibodies are used and at least one of said monoclonal antibodies cross reacts with TSH, HCG, and FSH to an extent of less than 1%.

13. Process of claim 8, wherein said monoclonal antibody is radioactively labelled.

14. Process of claim 8, wherein said monoclonal antibody is enzymatically labelled.

15. Process of claim 12, wherein said process comprises sandwich immunoassay.

16. Process of claim 8, wherein said monoclonal antibody comprises an Fab fragment.

17. Process of claim 13, wherein said label is $^{125}$I.

18. Process of claim 14, wherein said enzyme label is peroxidase or B-galactosidase.

19. Process of claim 8, wherein said antibody is fluorescently labelled.

20. Process of claim 12, comprising competitive immunoassay.

21. Process of claim 15, comprising forward sandwich immunoassay.

22. Process of claim 15 comprising simultaneous sandwich immunoassay.

23. Process of claim 15 comprising reverse sandwich immunoassay.

24. Reagent for the determination of the presence of luteinizing hormone (LH) comprising at least one monoclonal antibody of claim 4 and a buffer.

25. Reagent of claim 24, wherein said antibody cross reacts with TSH, HCG, and FSH to an extent of less than 1%.

26. Reagent of claim 24, comprising at least two monoclonal antibodies one of which cross reacts with TSH, HCG, and FSH to an extent of less than 1%.

27. Reagent of claim 24 comprising monoclonal antibodies MAB 369 or MAB 799.

28. Reagent of claim 26 comprising monoclonal antibodies MAB 369 and MAB 799.

29. A kit for determining presence of luteinzing hormone comprising separate components of reagents at least one of which is a first monoclonal antibody in accordance with claim 4 and another component which is a member selected from the group consisting of an antibody which specifically binds to the Fcγ part of said first monoclonal antibody and a labeled antibody which specifically binds to luteinising hormone.

30. A kit as in claim 29 wherein the first antibody specifically binds to luteinizing hormone and cross reacts with TSH, HCG, and FSH to an extent of less than 1%.

31. A kit as in claim 29 wherein said separate components are both monoclonal antibodies which specifically bind to luteinizing hormone.

32. Kit of claim 29 comprising monoclonal antibody MAB 369 or monoclonal antibody MAB 799.

33. Kit of claim 31 comprising monoclonal antibodies MAB 369 and MAB 799.

* * * * *